(12) United States Patent
Oohashi

(10) Patent No.: US 8,450,685 B2
(45) Date of Patent: May 28, 2013

(54) ELECTRON PROBE MICROANALYZER AND DATA PROCESSING METHOD IMPLEMENTED THEREIN

(75) Inventor: Hidemi Oohashi, Tokyo (JP)

(73) Assignee: JEOL Ltd., Tokyo (JP)

(*) Notice: Subject to any disclaimer, the term of this patent is extended or adjusted under 35 U.S.C. 154(b) by 0 days.

(21) Appl. No.: 13/347,868

(22) Filed: Jan. 11, 2012

(65) Prior Publication Data

US 2012/0181425 A1 Jul. 19, 2012

(30) Foreign Application Priority Data

Jan. 17, 2011 (JP) ................................ 2011-006935

(51) Int. Cl.
*H01J 37/26* (2006.01)
*A61B 6/03* (2006.01)
*G01B 11/14* (2006.01)

(52) U.S. Cl.
USPC ........... 250/309; 250/305; 250/306; 250/307; 250/311; 250/251; 356/369; 356/401

(58) Field of Classification Search
USPC .. 250/251, 305, 306, 307, 309, 311; 345/369, 345/401; 356/369, 401
See application file for complete search history.

(56) References Cited

U.S. PATENT DOCUMENTS

| | | | | |
|---|---|---|---|---|
| 3,440,422 A | * | 4/1969 | Ball et al. | 378/92 |
| 3,526,767 A | * | 9/1970 | Roth et al. | 378/31 |
| 4,481,651 A | * | 11/1984 | Haendle | 378/22 |
| 4,839,913 A | * | 6/1989 | Annis et al. | 378/44 |
| 5,659,174 A | * | 8/1997 | Kaneoka et al. | 250/310 |
| 5,866,905 A | * | 2/1999 | Kakibayashi et al. | 250/311 |
| 7,245,692 B2 | * | 7/2007 | Lu et al. | 378/4 |
| 7,349,090 B2 | * | 3/2008 | Wack et al. | 356/369 |
| 7,751,046 B2 | * | 7/2010 | Levy et al. | 356/401 |
| 8,173,983 B1 | * | 5/2012 | Sahadevan | 250/494.1 |
| 8,179,530 B2 | * | 5/2012 | Levy et al. | 356/401 |
| 8,247,769 B2 | * | 8/2012 | Zewail | 250/311 |
| 2011/0229947 A1 | * | 9/2011 | Zahn et al. | 435/161 |
| 2012/0156747 A1 | * | 6/2012 | Zahn et al. | 435/161 |
| 2012/0241611 A1 | * | 9/2012 | Kaji | 250/311 |

FOREIGN PATENT DOCUMENTS

| JP | 6231717 A | 8/1994 |
|---|---|---|
| JP | 2006125952 A | 5/2006 |

\* cited by examiner

*Primary Examiner* — David A Vanore
(74) *Attorney, Agent, or Firm* — The Webb Law Firm

(57) ABSTRACT

In an electron probe microanalyzer (EPMA) and a method of use thereof, even if plural sets of X-ray image data are obtained at different timings from regions between which a positional deviation occurs, processing for obtaining the correlation is performed precisely. The sets of X-ray image data are obtained from the same region of a sample using the EPMA at different timings and stored in memory along with sets of electron image data based on detection of secondary or backscattered electrons arising from the region. The sets of electron image data obtained at the different timings are compared, and the amount of positional deviation is calculated. An operation for extracting a region common to the regions respectively producing the sets of X-ray image data obtained at the different timings is performed on these sets of X-ray image data based on the calculated amount of positional deviation.

4 Claims, 4 Drawing Sheets

| SEQUENCE | WDS CH1 | WDS CH2 | WDS CH3 | WDS CH4 | WDS CH5 | SECONDARY ELECTRON IMAGE |
|---|---|---|---|---|---|---|
| 1 | ELEMENT A | ELEMENT C | ELEMENT D | ELEMENT E | ELEMENT F | Z1 |
| 2 | ELEMENT B | ELEMENT G | ELEMENT H | ELEMENT I | ELEMENT J | Z2 |

| SEQUENCE | WDS CH1 | WDS CH2 | WDS CH3 | WDS CH4 | WDS CH5 | SECONDARY ELECTRON IMAGE |
|---|---|---|---|---|---|---|
| 1 | ELEMENT A | ELEMENT C | ELEMENT D | ELEMENT E | ELEMENT F | Z1 |
| 2 | ELEMENT B | ELEMENT G | ELEMENT H | ELEMENT I | ELEMENT J | Z2 |

ELECTRON PROBE MICROANALYZER AND DATA PROCESSING METHOD IMPLEMENTED THEREIN

BACKGROUND OF THE INVENTION

1. Field of the Invention

The present invention relates to an electron probe microanalyzer (EPMA) and, more particularly, to improvements in a method of performing data processing on plural sets of X-ray image data (such as a processing subroutine for creating a scatter diagram) obtained from the same region of a sample.

2. Description of Related Art

In electron probe microanalysis (EPMA), a sample is irradiated with a sharply focused electron beam. The wavelength and strength of characteristic X-rays emanating from the sample are measured by a wavelength-dispersive X-ray spectrometer (WDS). Chemical elements contained in a quite small region of the sample are analyzed qualitatively or quantitatively. By fixing the WDS detection wavelength at the characteristic X-rays of a certain element and scanning the electron beam across the analyzed region of the sample in two dimensions, X-ray image data (mapping data) indicating a distribution of the certain element in the analyzed region can be obtained. The number of WDS units simultaneously installed in an instrument can be increased up to about five (5 channels) according to the need. Where five WDS units are installed, X-ray image data about five chemical elements can be obtained in one measurement.

FIG. 1 shows the configuration of a related art EPMA. The EPMA has an electron gun 1 producing an electron beam EB, a condenser lens system 2 for sharply focusing the beam EB onto a sample 3, and beam scanning coils 4 for scanning the beam EB over the sample 3 or directing the beam at an arbitrary position on the sample.

Secondary electrons produced from the sample 3 are detected by a secondary electron detector 5. A secondary electron signal processing circuit 6 receives the output from the detector 5, performs given processing on the signal (such as given amplification and A/D conversion), and sends the result to a control circuit 12. Characteristic X-rays emanating from the sample 3 are detected by a WDS (wavelength-dispersive spectrometer) 7 which is configured including a spectrometer 8 for spectrally dispersing the characteristic X-rays, an X-ray detector 9 for detecting the dispersed X-rays, a spectrometer control portion 10 for driving the spectrometer 8 to perform wavelength scanning or specifying a detected wavelength, and an X-ray signal processing circuit 11 receiving the output signal from the X-ray detector 9 indicating the detected X-rays, performing given processing (such as amplification and AID conversion) on the signal, and sending the result to the control circuit 12.

The control circuit 12 controls the spectrometer control portion 10. In addition, the control circuit stores the output signal from the X-ray signal processing circuit 11 indicating the detected characteristic X-rays into a data memory 13, sends the stored data to a data processing means 14 such that the data is analyzed or otherwise processed, and sends the results of the analysis and various kinds of image data to a display portion 15, where the results and data are displayed. The control circuit 12 and data processing means 14 are composed, for example, of a computer 16.

In the instrument constructed in this way, when an X-ray image of element A is obtained from a specified analyzed region, the control circuit 12 drives the spectrometer 8 via the spectrometer control portion 10 such that the characteristic X-rays of the element A to be analyzed impinge on the detector 9 and become detected. Under this condition, the electron beam is scanned over the specified analyzed region of the sample 11 by the beam scanning coils 4. The control circuit 12 stores the output signal from the X-ray detector 9 that indicates the detected X-rays into the data memory 13 such that the signal is correlated with the scan position. As a result, two-dimensional X-ray image data indicating a distribution of the element A in the specified analyzed region is obtained in the data memory 13.

Where X-ray images of two elements A and B need to be acquired from the same specified region, the spectrometer 8 is so set up that the characteristic X-rays of the element B impinge on the detector 9 and become detected. A sequence of operations for obtaining X-ray image data is performed once more.

In the foregoing description, a single WDS unit is mounted. Where the EPMA is equipped with five WDS units as described previously, if the five WDS units are all used, X-ray image data about the five elements can be obtained at a time. If two sequences of operations are performed, X-ray image data about 10 elements at maximum can be derived.

Phase analysis is available as one analysis technique based on X-ray image data about plural elements obtained from the same analyzed region in this way. Using X-ray image data about the elements, the correlation and compositional ratios between the elements can be examined. FIG. 5 shows one example of scatter diagram created using X-ray image data about iron (Fe) and silicon (Si). The scatter diagram is created by obtaining X-ray image data about each of the two elements consisting, for example, of 256×256 pixels and plotting the data (256×256 pixels) indicating X-ray intensity or concentration of Si versus the X-ray intensity or concentration of Fe.

Often, it takes long to obtain X-ray image data. If this is repeated as a sequence of steps, it will take longer to obtain X-ray images. If a sequence of measurements' is performed over a long time, the analyzed region might slightly shift between the first and second sequences of steps due to temperature variations or sample stage drifts.

Where the scatter diagram is created from X-ray image data about two elements, the essential premise behind this technique is that the two sets of X-ray image data have been derived from the same analyzed region. Therefore, if the regions giving rise to the sets of X-ray image data about the two elements deviate, the reliability of the scatter diagram deteriorates greatly.

In a case where X-ray image data about two elements are obtained by the same sequence of steps, it follows that data have been derived from the same region by simultaneous measurements. Consequently, the resulting scatter diagram has no problem. However, in a case where two sets of data are obtained by different sequences of steps and deviation between the regions cannot be neglected, the reliability of the scatter diagram will decrease greatly. This problem has become more conspicuous as the resolution of EPMA has been enhanced in recent years and X-ray image data have been obtained at higher resolution on increasing occasions.

SUMMARY OF THE INVENTION

In view of the foregoing problem, the present invention has been made. It is an object of the present invention to provide a method of processing X-ray image data in such a way that X-ray images can be obtained from the same region if different sequences of steps are used. It is another object of the invention to provide an electron probe microanalyzer implementing this method.

To achieve these objects, the present invention is configured in the manner as described below.

(1) A first embodiment of the present invention provides a method of processing X-ray image data by obtaining sets of X-ray image data from the same region of a sample at different timings using an electron probe microanalyzer and storing the sets of X-ray image data into memory. Sets of electron image data based on detection of secondary electrons or backscattered electrons emanating from the region are also obtained at the aforementioned timings and stored in memory. The sets of electron image data obtained at the different timings are compared. An amount of positional deviation is calculated. Based on the calculated amount of positional deviation, an operation for extracting a region common to regions respectively producing the sets of the X-ray image data obtained at the different timings is performed.

(2) A second embodiment of the present invention is based on the first embodiment and further characterized in that the calculation of the amount of positional deviation from the sets of electron image data obtained at the different timings is carried out by Fourier transform.

(3) A third embodiment of the present invention is based on the first or second embodiment and further characterized in that the scatter diagram is created based on sets of X-ray image data obtained after performing the operation for extracting the region common to the regions respectively producing the sets of X-ray image data.

(4) A fourth embodiment of the invention provides an electron probe microanalyzer for obtaining plural sets of X-ray image data from the same region of a sample at different timings and storing the sets of data in memory. The microanalyzer has: means for obtaining sets of electron image data based on detection of secondary electrons or backscattered electrons emanating from the same region at the aforementioned timings simultaneously with the sets of X-ray image data and storing the sets of electron image data in memory; computing means for comparing the sets of electron image data obtained at the different timings and calculating an amount of positional deviation; and data processing means for performing an operation for extracting a region common to regions respectively producing the sets of the X-ray data obtained at the different timings on these sets of X-ray data based on the calculated amount of positional deviation.

The present invention yields the following advantageous effects.

(1) According to the first embodiment of the present invention, in a case where X-ray image data are obtained from the same region at different timings and stored in memory, secondary electron images or backscattered electron images of the region are obtained at the aforementioned timings. The sets of electron image data obtained at the different timings are compared and an amount of positional deviation is calculated. An operation for extracting a region common to regions respectively producing the sets of X-ray image data is performed. Thus, X-ray images of the same region can be obtained even if different sequences of step are performed.

(2) According to the second embodiment, the amount and direction of the positional deviation between the secondary electron images or backscattered electron images indicated by electron image data are calculated by FFT (fast Fourier transform).

(3) According to the third embodiment, a scatter diagram is created based on X-ray image data about a region common to regions respectively producing the extracted sets of X-ray image data. Consequently, an accurate scatter diagram free of the effects of positional deviation can be obtained.

(4) According to the fourth embodiment, an EPMA (electron probe microanalyzer) is provided which obtains X-ray image data from the same region of a sample at different timings and which stores the data in memory. The EPMA has the means for simultaneously obtaining sets of electron image data based on detection of secondary electrons or backscattered electrons emanating from the same region at the aforementioned timings and storing the sets of data, the computing means for comparing the sets of electron image data obtained at the different timings and calculating the amount of positional deviation, and the data processing means for performing an operation for extracting a region common to regions respectively producing the sets of X-ray image data obtained at the different timings based on the calculated amount of positional deviation. Thus, the EPMA can obtain X-ray images of the same region from the plural X-ray images obtained using different sequences of steps.

DESCRIPTION OF THE PREFERRED EMBODIMENTS

Figures 1, 2:
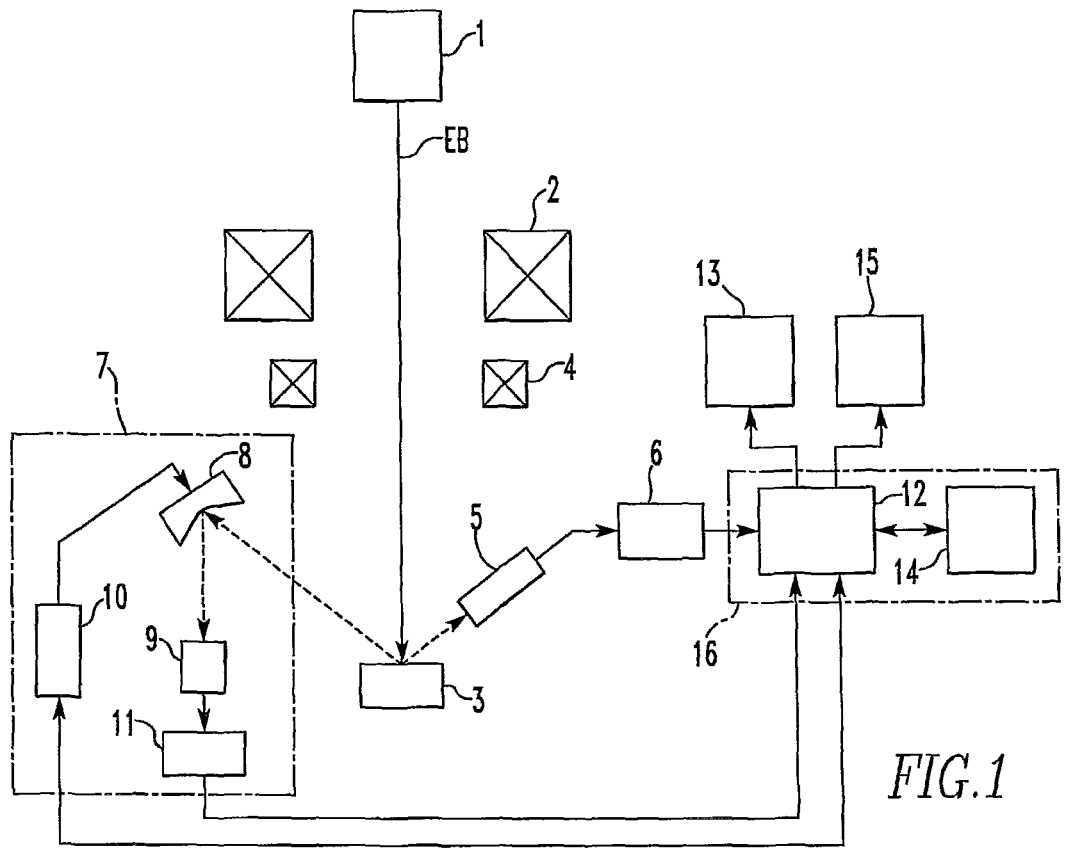
FIG. 1 is a block diagram of a related art instrument and an instrument according to one embodiment of the present invention.
FIG. 2 is a table illustrating the contents of a data memory in which secondary electron image data and X-ray image data are stored.

The preferred embodiments of the present invention are hereinafter described in detail with reference to the drawings. FIG. 1 is a block diagram showing an instrument according to one embodiment of the present invention. This inventive instrument is similar to the related art instrument which has been already described also in connection with FIG. 1 except that secondary electron image data are obtained simultaneously with the acquisition of the X-ray image data in the sequence of steps and stored in memory in association with the sequence of steps and that data processing is performed by the data processing means 14 by utilizing the secondary electron image data. The operation of the instrument according to the invention is described below.

In FIG. 1, the electron beam EB produced from the electron gun 1 is sharply focused onto the sample 3 by the condenser lens system 2. The beam is scanned over the sample 3 by the beam scan coils 4 or directed at an arbitrary position on the sample.

Secondary electrons, backscattered electrons, and characteristic X-rays are produced from the beam position on the sample 3. The secondary electrons are detected by the secondary electron detector 5. The output signal from the detector 5 indicating the detected secondary electrons is amplified, converted into digital form, or otherwise processed by the secondary electron signal processing signal 6, and sent to the control circuit 12. Then, the data is stored in the ancillary data memory 13.

On the other hand, the characteristic X-rays are detected by the WDS 7 which is configured including the spectrometer 8 for spectrally dispersing the characteristic X-rays, the X-ray detector 9 for detecting the dispersed X-rays, the spectrometer control portion 10 for driving the spectrometer 8 and performing wavelength scanning or specifying a detection wavelength, and the X-ray signal processing circuit 11 for amplifying the output from the detector 9 indicating the detected X-rays, converting the analog signal into digital form, or otherwise processing the signal, and sending the result to the control circuit 12. The signal sent from the X-ray signal processing circuit 11 to the control circuit 12 is stored in the ancillary data memory 13.

The control circuit 12 controls the whole EPMA. This control operation includes controlling of the spectrometer control portion 10. In addition, the control portion 12 sends data, which have been obtained by measurements and stored in the data memory 13, to the data processing means 14, where the data are analyzed. The results and various image data are sent to the display portion 15 and displayed.

As described previously, in a case where an X-ray image of chemical element A is obtained from a specified analyzed region by a first sequence of steps, the control circuit 12 controls the spectrometer control portion 10 to drive the spectrometer 8 such that the characteristic X-rays of the target element A impinge on the detector 9 and become detected. Under this condition, the electron beam is scanned over the specified analyzed region of the sample 11 by the beam scan coils 4. The output signal from the X-ray detector 9 indicating the detected X-rays is stored in the data memory 13 by the control circuit 12 such that the signal is correlated with the scan position. As a result, X-ray image data indicating a distribution of the element A in the specified analyzed region is obtained in the data memory 13. During this first sequence of steps, secondary electron image data Z1 obtained at the same time is stored in the data memory 13.

In a case where an X-ray image of an element B is obtained from the same specified analyzed region by a second sequence of steps, the spectrometer 8 is so set that the characteristic X-rays of the element B impinge on the detector 9 and become detected again. X-ray image data indicating a distribution of the element B in the specified analyzed region is obtained. During this second sequence of steps, secondary electron image data Z2 obtained at the same time is stored in the data memory 13.

As a result, when the second sequence of step ends, sets of X-ray image data indicating the distributions of the elements A and B, respectively, in the specified analyzed region, the secondary electron image data Z1 obtained by the first sequence of steps, and the secondary electron image data Z2 obtained by the second sequence of steps are stored in the data memory 13. In the foregoing case, there is a single WDS unit. In the case of an EPMA having five WDS units, X-ray image data about up to five elements can be obtained by one sequence of steps. X-ray image data about up to ten elements can be obtained by two sequences of steps. These data are stored, for example as shown in FIG. 2, in the data memory 13 such that the data are correlated with the sequence of steps and with the WDS channels.

Figure 3:
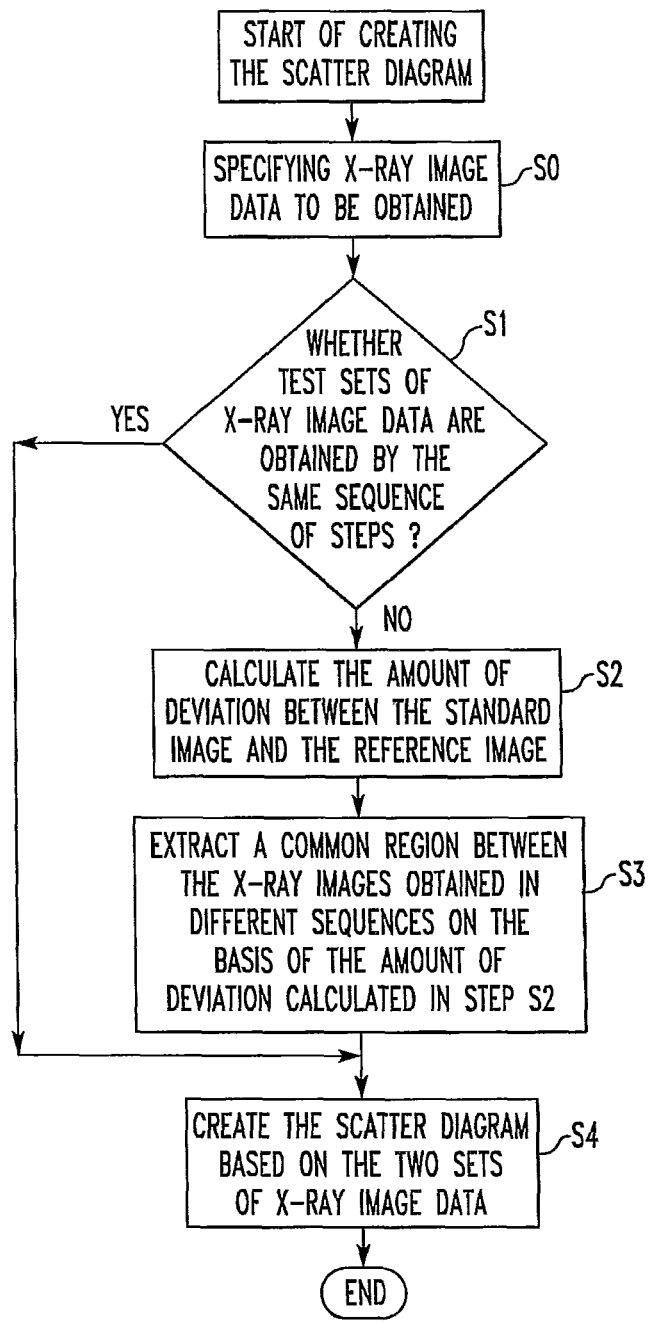
FIG. 3 is a flowchart illustrating a sequence of steps performed by the instrument according to the invention.

FIG. 3 is a flowchart illustrating a sequence of data processing steps performed by the data processing means 14 to create a scatter diagram. In the following description, it is assumed that the EPMA is equipped with 5 WDS units and that X-ray image data about 10 elements including the elements A and B are stored in the data memory 13 as shown in FIG. 2.

When a processing subroutine for creating the scatter diagram begins, the user (human operator) is required to specify two elements for which the scatter diagram should be created such that X-ray image data about the elements are obtained (step S0).

When the operator specifies the elements A and B, for example, from among the 10 elements using an input device (not shown), a check is made as to whether sets of X-ray image data about the specified elements A and B, respectively, are data obtained by the same sequence of steps (step S1).

Figure 4A:
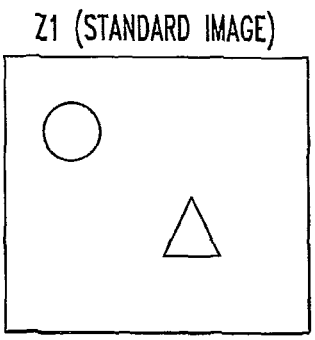
FIG. 4 illustrates the manner in which amounts of positional deviations are calculated based on secondary electron image data and in which two sets of X-ray image data are processed based on the amounts of positional deviations.
Figure 4B:
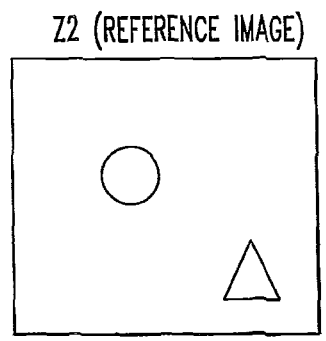

For example, in a case where the data have been obtained by the same sequence of steps (such as data about the elements A and C or data about the elements B and G), the aforementioned positional deviation does not occur and, therefore, control directly proceeds to step S4, where the processing subroutine is performed using the sets of X-ray image data about either the elements A and C or the elements B and G to create a scatter diagram. In the case of data arising from the elements A and B, the data have not been obtained by the same sequence of steps and so control goes to step S2, where the secondary electron image data Z1 obtained simultaneously in the first sequence of steps in which the X-ray image data about the element A was obtained and the secondary electron image data Z2 obtained by the second sequence of steps in which the X-ray image data about the element B was obtained are read from the data memory 13 as shown in FIGS. 4A and 4B.

It is assumed, for example, that Z1 is a standard image and Z2 is a reference image. The amount of deviation between the two secondary electron images is calculated. Since a secondary electron image well reflects the surface topography, the amount of deviation can be precisely found using secondary electron images. Obviously, the amount of deviation can be found using backscattered electron images obtained using backscattered electron detectors.

Figure 4C:
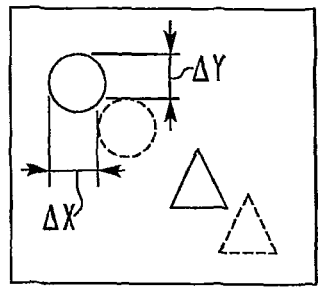

An existing technique such as computation of a correlation is used as a method of finding the amount of deviation. For example, FFT (fast Fourier transform) is used. If FFT is performed, the amounts of deviations $\Delta X$ and $\Delta Y$ of the reference image Z2 in the directions of X and Y directions, respectively, taken with respect to the standard image Z1 are found as shown in FIG. 4C. Data about the found amounts of deviations $\Delta X$ and $\Delta Y$ are stored in the data memory 13.

Figure 4D:
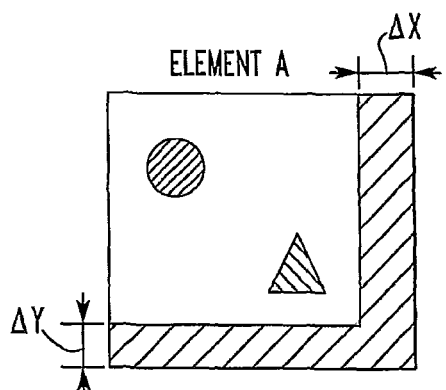
Figure 4E:
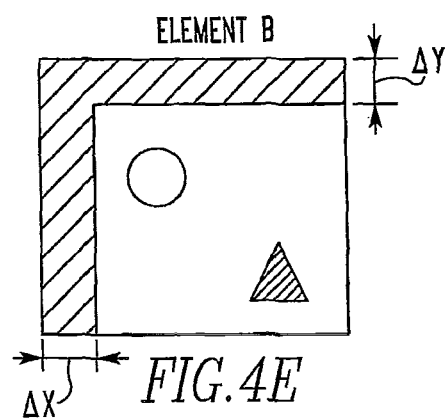

In the next step S3, a region common to regions respectively producing the X-ray image data about the element A and the X-ray image data about the element B is extracted from these two sets of data using data about the amounts of deviations $\Delta X$ and $\Delta Y$ obtained based on the secondary electron images. In particular, with respect to the data read from the data memory 13 (i.e., the X-ray image data about the element A shown in FIG. 4D and the X-ray image data about the element B shown in FIG. 4E), the hatched right-end portion $\Delta X$ and lower-end portion $\Delta Y$ which are not present in the region indicated by the X-ray image data about the element B are deleted from the X-ray image data about the element A, and the hatched left-end portion $\Delta X$ and upper-end portion $\Delta Y$ not present in the region indicated by the X-ray image data about the element A are deleted from the X-ray image data about the element B, using the data about the amounts of deviations $\Delta X$ and $\Delta Y$.

Figure 4F:
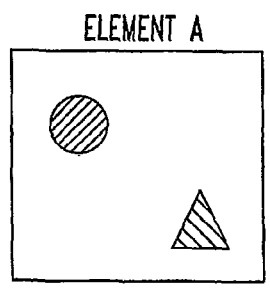
Figure 4G:
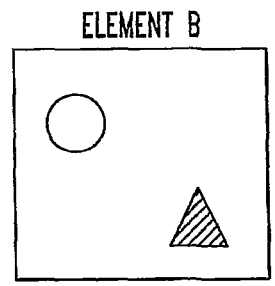
Figure 5:
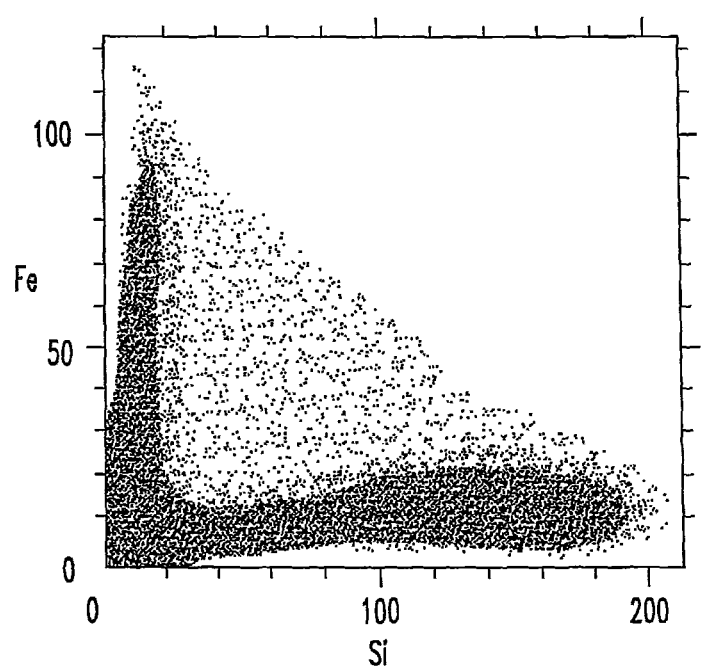
FIG. 5 is a scatter diagram.

As a result, as shown in FIGS. 4F and 4G, the region common to the regions respectively producing the two sets of X-ray image data is left (i.e., data about the common region remain) though the area is reduced by amounts corresponding to the deleted regions. Based on the two sets of X-ray image data, the processing subroutine for creating a scatter diagram is performed at step S4. Since the regions indicated by the two sets of X-ray image data and undergoing the processing subroutine for creating a scatter diagram are coincident, the scatter diagram is created correctly.

Secondary electron images and backscattered electron images carry much greater amounts of surface information than X-ray images and provide higher resolution. Therefore, it is possible to calculate amounts of deviations correctly.

As described in detail so far, the present invention makes it possible to precisely extract a region common to regions respectively producing X-ray images obtained by plural sequences of steps and to correctly perform correlation processing such as the processing subroutine for creating a scatter diagram.

Having thus described my invention with the detail and particularity required by the Patent Laws, what is desired protected by Letters Patent is set forth in the following claims.

The invention claimed is:

1. A method of processing X-ray image data in an electron probe microanalyzer, said method comprising the steps of:
   obtaining plural sets of X-ray image data from the same region of a sample at different timings using the electron probe microanalyzer and storing the sets of X-ray image data into memory;
   simultaneously obtaining sets of electron image data based on detection of secondary electrons or backscattered electrons emanating from said region at said timings and storing the sets of electron image data into memory;
   comparing the sets of electron image data obtained at the different timings and calculating an amount of positional deviation; and
   performing an operation for extracting a region common to regions respectively producing the sets of X-ray image data obtained at said different timings on these sets of X-ray image data based on the calculated amount of positional deviation.

2. A method of processing X-ray image data in an electron probe microanalyzer as set forth in claim 1, wherein the calculation of the amount of positional deviation from the sets of electron image data obtained at said different timings is carried out by Fourier transform.

3. A method of processing X-ray image data in an electron probe microanalyzer as set forth in any one of claim 1 or 2, wherein the scatter diagram is created based on sets of X-ray image data obtained after performing the operation for extracting the region common to the regions respectively producing the sets of X-ray image data.

4. An electron probe microanalyzer for obtaining plural sets of X-ray image data from the same region of a sample at different timings and storing the sets of data into memory, said electron probe microanalyzer comprising:
   means for obtaining plural sets of electron image data based on detection of secondary electrons or backscattered electrons emanating from said same region at said timings simultaneously with corresponding sets of X-ray image data and storing the sets of electron image data in memory;
   data processing means programmed with steps for comparing the sets of electron image data obtained at the different timings and calculating an amount of positional deviation; and
   said data processing means further programmed for extracting a common region from the sets of X-ray image data obtained at the different timings based on the calculated amount of positional deviation.

\* \* \* \* \*